United States Patent [19]
Albrecht et al.

[11] Patent Number: 5,908,393
[45] Date of Patent: Jun. 1, 1999

[54] REDUCING NOISE IN A BIOLOGICAL SIGNAL

[75] Inventors: Paul Albrecht, Bedford; Paul G. Grimshaw, Acton; Kevin S. Librett, Natick; Jeffrey M. Arnold, Wellesley, all of Mass.

[73] Assignee: Cambridge Heart, Inc., Bedford, Mass.

[21] Appl. No.: 09/071,834

[22] Filed: May 4, 1998

[51] Int. Cl.$^6$ .................................................. A61B 5/0402
[52] U.S. Cl. ............................................. 600/509; 128/901
[58] Field of Search ............................ 128/901; 600/509, 600/511, 508

[56] References Cited

U.S. PATENT DOCUMENTS

| | | | |
|---|---|---|---|
| 4,038,536 | 7/1977 | Feintuch | 235/152 |
| 4,760,540 | 7/1988 | Yuen | 364/724 |
| 4,781,201 | 11/1988 | Wright et al. | 128/671 |
| 4,783,660 | 11/1988 | Pierce | 342/101 |
| 4,802,491 | 2/1989 | Cohen et al. | 128/702 |
| 4,979,110 | 12/1990 | Albrecht et al. | 364/413.83 |
| 5,146,926 | 9/1992 | Cohen | 128/710 |
| 5,209,237 | 5/1993 | Rosenthal | 128/698 |
| 5,259,387 | 11/1993 | dePinto | 128/696 |
| 5,265,617 | 11/1993 | Verrier et al. | 128/704 |
| 5,323,783 | 6/1994 | Henkin et al. | 128/703 |
| 5,421,342 | 6/1995 | Mortara | 128/696 |
| 5,521,851 | 5/1996 | Wei et al. | 364/574 |

OTHER PUBLICATIONS

Simoons et al., "On–Line Processing of Orthogonal Exercise Electrocardiograms," Computers and Biomedical Research, vol. 8 (1975), pp. 105–117.
Ferrara et al., "The Time–Sequenced Adaptive Filter", IEEE Trans. Acoust., Speech and Sig. Proc., vol. 29 (1981), pp. 679–683.
Frank et al., "Adaptive Filtering in ECG Monitoring of the Fetal Heart Rate," J. Electrocardiology, Suppl. Issue, pp. 108–113 (Oct. 1987).
Lander et al., "Performance Assessment of Optimal Filtering of the High Resolution Electrocardiogram", In: Computers in Cardiology, IEEE Computer Society Press, Los Alamitos, CA (1994), pp. 693–695.
Lander et al., "Principles and Signal Processing Techniques of the High–Resolution Electrocardiogram," Prog. Cardiovasc. Dis. vol. 35(3) (1992), pp. 169–188.
Meyer et al., "Electrocardiogram Baseline Noise Estimation and Removal Using Cubic Splines and State–Space Computation Techniques," Computers and Biomedical Research 10, pp.459–470 (1977).
Mortara, "Source Consistency Filtering—Application to Resting ECGs," J. Electrocardiology, vol. 25 Supplement, pp. 200–206 (1992).
Mortara, "Source Consistency Filtering—A New Tool for ECG Noise Reduction," IEEE, pp. 125–128 (1992).
Wei et al., "A New Method for Reducing Signal–Overlapping Noise in Standard Electrocardiogram," Proceedings of Computers in Cardiology, pp. 795–797 (1993).
Wildrow, "Adaptive Interference Canceling," Adaptive Signal Processing, Applications Part IV, Chap. 12, Prentice-–Hall, Englewood Cliffs, NJ, pp. 302–367 (1985).

*Primary Examiner*—Scott M. Getzow
*Attorney, Agent, or Firm*—Fish & Richardson PC

[57] ABSTRACT

A method of reducing noise in a biological signal, such as an ECG signal, includes acquiring a biological signal, comparing the biological signal to a representative signal, and generating a predicted signal corresponding to the representative signal when the biological signal sufficiently matches the representative signal. The predicted signal is subtracted from the biological signal to produce a second signal, and a filter is applied to the second signal to produce a filtered signal. The predicted signal and the filtered signal then are combined to produce a noise-reduced signal.

31 Claims, 5 Drawing Sheets

|⊢———⊣|
1 SECOND

REDUCING NOISE IN A BIOLOGICAL SIGNAL

TECHNICAL FIELD

The invention relates to reducing noise in an electrocardiogram ("ECG") or other biological signal.

BACKGROUND

Biological signals may include substantial amounts of noise. For example, muscular activity is a major source of noise ("muscle noise") in ECG signals. Muscle noise usually appears as rapid, wavy deflections that render the ECG difficult to read.

Simple filters may be used to remove the high frequencies associated with muscle noise from an ECG signal. An example of such a filter is a low-pass filter with a cut-off frequency near 25 Hz. Simple filters such as low pass filters may have the unwanted property of distorting the underlying ECG signal, since the frequency content of the underlying ECG signal may overlap that of muscle noise. For example, the QRS complex of the ECG signal, which corresponds electrically to depolarization of the ventricles of the heart, has frequency content that overlaps muscle noise.

Other noise reduction methods seek to avoid the problem of distorting the QRS complex. One such method employs a filter system that changes the cutoff frequency of the filter during the QRS complex of the ECG signal. The system detects the presence of a QRS complex in the ECG signal and switches the filter to a higher cutoff frequency during the QRS complex. The system switches the filter back to a lower cutoff frequency after the QRS complex ends.

Another system processes multiple ECG signals. These signals are highly redundant in that they arise from a single three-dimensional ECG source (i.e., the heart). The system exploits the redundancy by computing coefficients that allow an input signal to be predicted from the other input signals and using the coefficients to compute a predicted input signal. Next, the system generates a compliance factor that indicates the correspondence between the input signal and the corresponding predicted signal for each time sample of the signals. The system then uses the compliance factor in filtering the input signal.

Another system filters an input signal to create a basic signal and a residual signal, where the basic signal corresponds to a low-pass-filtered portion of the input signal and the residual signal corresponds to the remainder of the input signal. The system then uses redundant signals from multiple points to generate parameters that the system uses to build a signal that the system compares to the residual signal to determine a noise index. The system uses the noise index to scale the residual signal. Finally, the system combines the basic signal and the scaled residual signal to form a filtered version of the input signal.

SUMMARY

Noise may be removed from a biological signal by separating an input signal into a predicted signal and a second signal. In general, the predicted signal includes a component of the input signal that is known or can be estimated using other available information. When the biological signal is a generally periodic signal, such as an ECG signal, the predicted signal may be generated from previous periods (e.g., previous beats) of the biological signal. The predicted signal also may be generated from related biological signals (e.g., the predicted signal for an ECG lead may be generated from the signals produced by other ECG leads).

While the predicted signal generally includes only low levels of noise, the second signal generally includes higher levels of noise. The second signal is filtered to reduce the noise and then is combined with the predicted signal to produce a low noise output signal. Since filtering is not applied to features of the biological signal which are known with a higher level of confidence (i.e., features included in the predicted signal), the technique is well suited for removing high frequency noise, such as muscle noise, from an ECG signal, while preserving the high frequency components of the QRS complex of the ECG signal.

Noise reduction is of particular importance in applications that attempt to measure low level ECG features such as ST segment changes, P waves, or the fetal ECG, and of even more importance in applications that attempt to measure microvolt level features of the ECG, such as electrical alternans, His-Purkinje activity, and late potentials such as might be measured by a signal averaged ECG (SAECG).

In one general aspect, noise is reduced in an acquired biological signal, such as an ECG signal. A predicted signal corresponding to a representative signal is generated and subtracted from the biological signal to produce a second signal. Thereafter, a filter is applied to the second signal to produce a filtered signal that is combined with the predicted signal to produce a noise-reduced signal.

Embodiments may include one or more of the following features. The biological signal may be compared to the representative signal, and the predicted signal may be generated based on results of the comparison. A set of representative signals corresponding to different groups or clusters of biological signals, such as ECG signals having different beat morphologies, may be maintained. The biological signal may be compared to a representative signal for each group of biological signals to select a best-matching representative signal. The predicted signal then may be generated using the best-matching representative signal. The best-matching representative signal may be modified using the biological signal.

The predicted signal may be generated as corresponding to the representative signal when the biological signal sufficiently matches the representative signal. When the biological signal does not sufficiently match the representative signal, a predicted signal corresponding to the biological signal may be generated. A representative signal corresponding to the biological signal also may be generated.

The procedure may be performed with respect to a particular portion of the biological signal (e.g., with respect to a particular beat). In this case, the representative beat may correspond to at least one portion (e.g., one or more beats) of the biological signal that precedes the particular portion. The representative signal also may correspond to one or more signals related to the biological signal. For example, when the biological signal is an ECG signal, the representative signal may be based on other ECG leads.

The filter may be a low pass filter, such as a sixth order Bessel filter with a cutoff frequency of, for example, 15 Hz When the biological signal is an ECG signal, a QRS complex of a beat of the ECG signal may be detected. This QRS complex then is compared to a QRS complex of the representative signal. When they match sufficiently, the predicted signal may be generated as having a QRS complex corresponding to the QRS complex of the representative signal. For example, the predicted signal may have a QRS complex corresponding to the QRS complex of the representative signal and a constant value (e.g., zero) at all other points.

The techniques may be implemented in computer hardware or software, or a combination of the two. However, the techniques are not limited to any particular hardware or software configuration; they may find applicability in any computing or processing environment that may be used for processing biological signals. Preferably, the techniques are implemented in computer programs executing on programmable computers that each include a processor, a storage medium readable by the processor (including volatile and non-volatile memory and/or storage elements), at least one input device, and one or more output devices. Program code is applied to data entered using the input device to perform the functions described and to generate output information. The output information is applied to the one or more output devices.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage medium or device (e.g., CD-ROM, hard disk or magnetic diskette) that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other features and advantages will be apparent from the following description, including the drawings and the claims.

DETAILED DESCRIPTION

Figure 1:
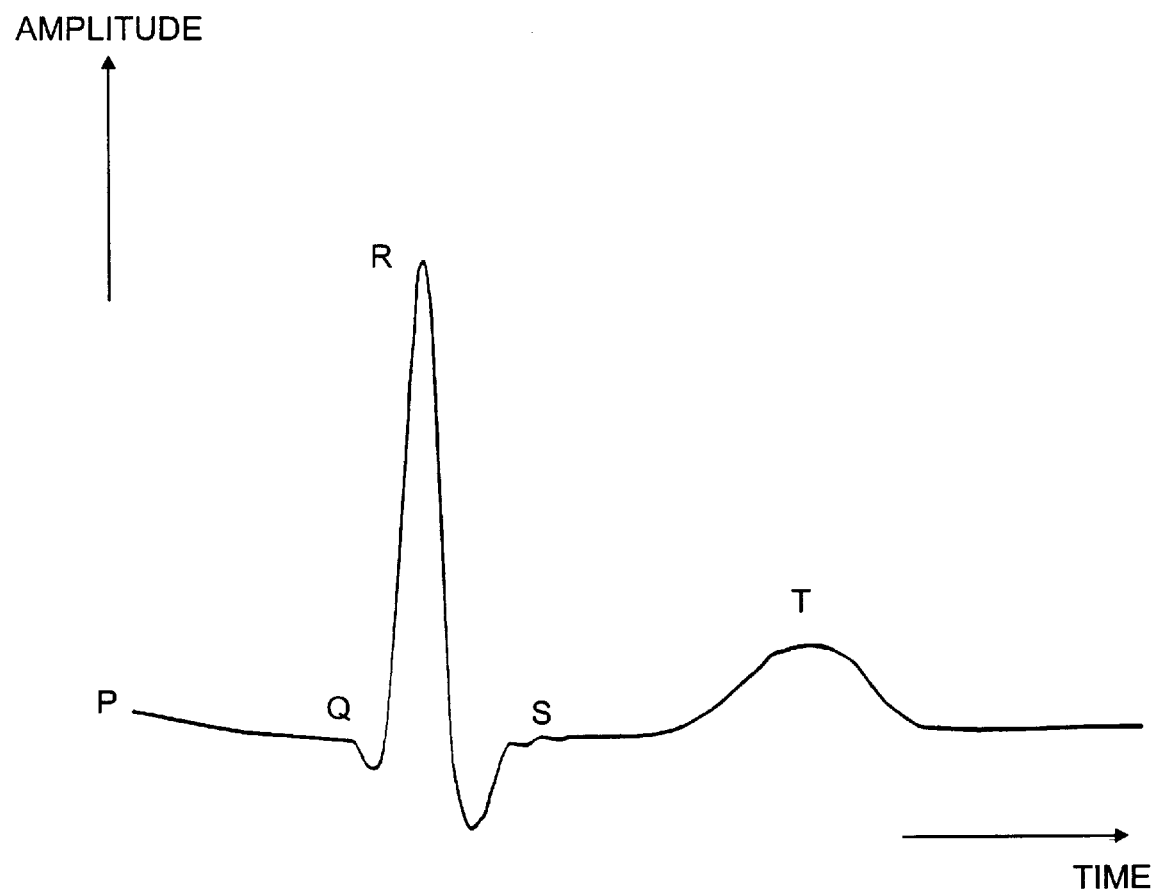
FIG. 1 is a schematic representation of an ECG waveform.

Referring to FIG. 1, an ECG waveform for a single beat is typically referred to as a PQRST complex. Briefly, the P wave appears at initiation of the beat and corresponds to activity in the atria, while the QRST complex follows the P wave and corresponds to ventricular activity. The QRS component represents the electrical activation of the ventricles, while the T wave represents their electrical recovery. The ST segment is a relatively quiescent period.

Figure 2:
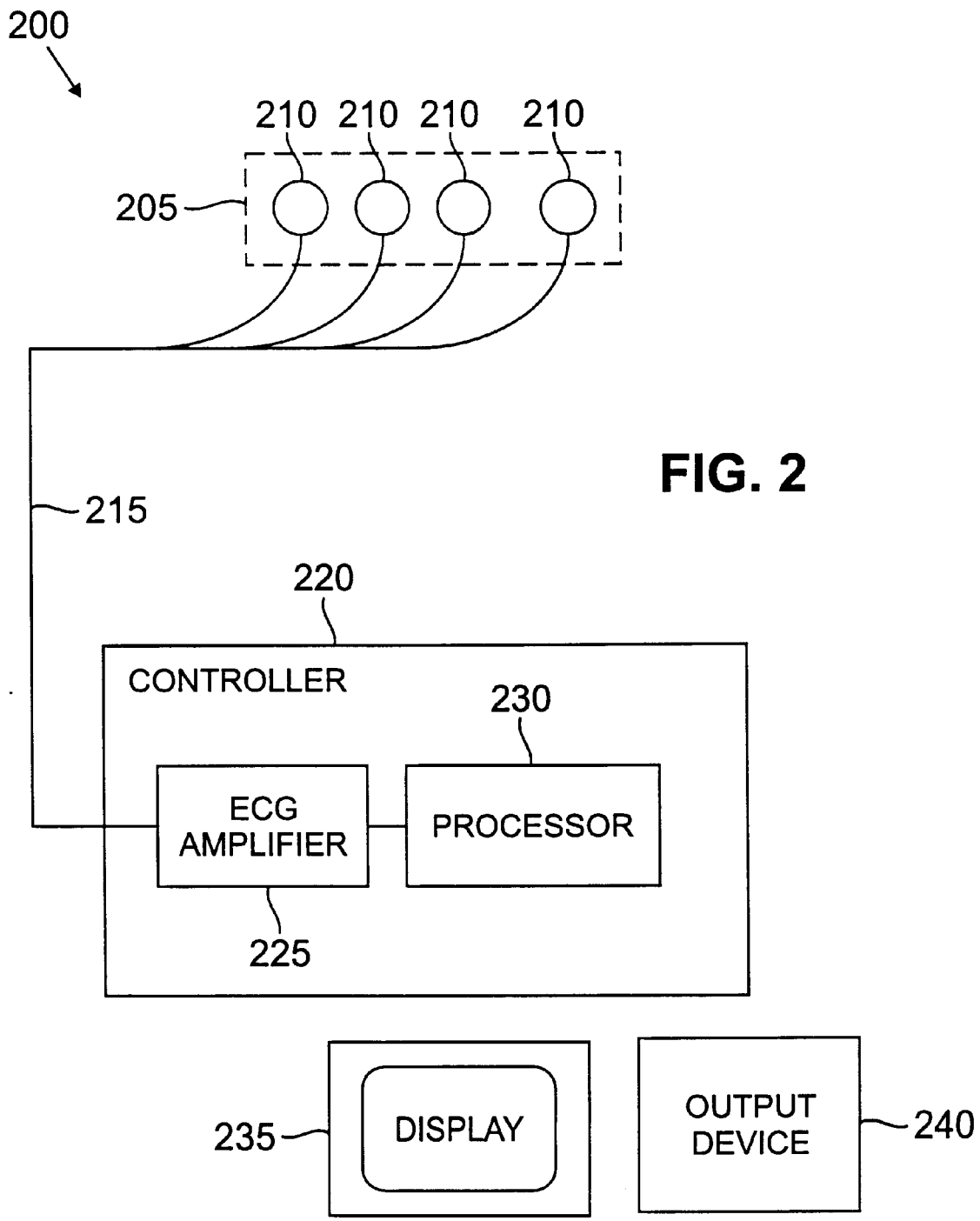
FIG. 2 is a block diagram of an ECG system.

Referring to FIG. 2, an ECG system 200 includes a set 205 of electrodes 210. The electrodes may be standard ECG electrodes, or may be an array of electrodes applied to cover the anterior, lateral and posterior areas of the torso. The electrodes function separately from one another, but may be physically affixed together to form a flexible band or other arrangement. The system 200 further includes a set of leads 215 that connect the electrodes to a system controller 220.

The controller includes an ECG amplifier module 225 and a processor 230. The module 225 receives analog signals from the leads 215 and provides digital signals to the processor 230. The processor 230 processes the conditioned signals to produce results that the processor then provides to a connected display 235 or to an output device 240, such as a printer. The displayed results may include filtered ECG signals displayed in a time-synchronized manner.

Figure 3:
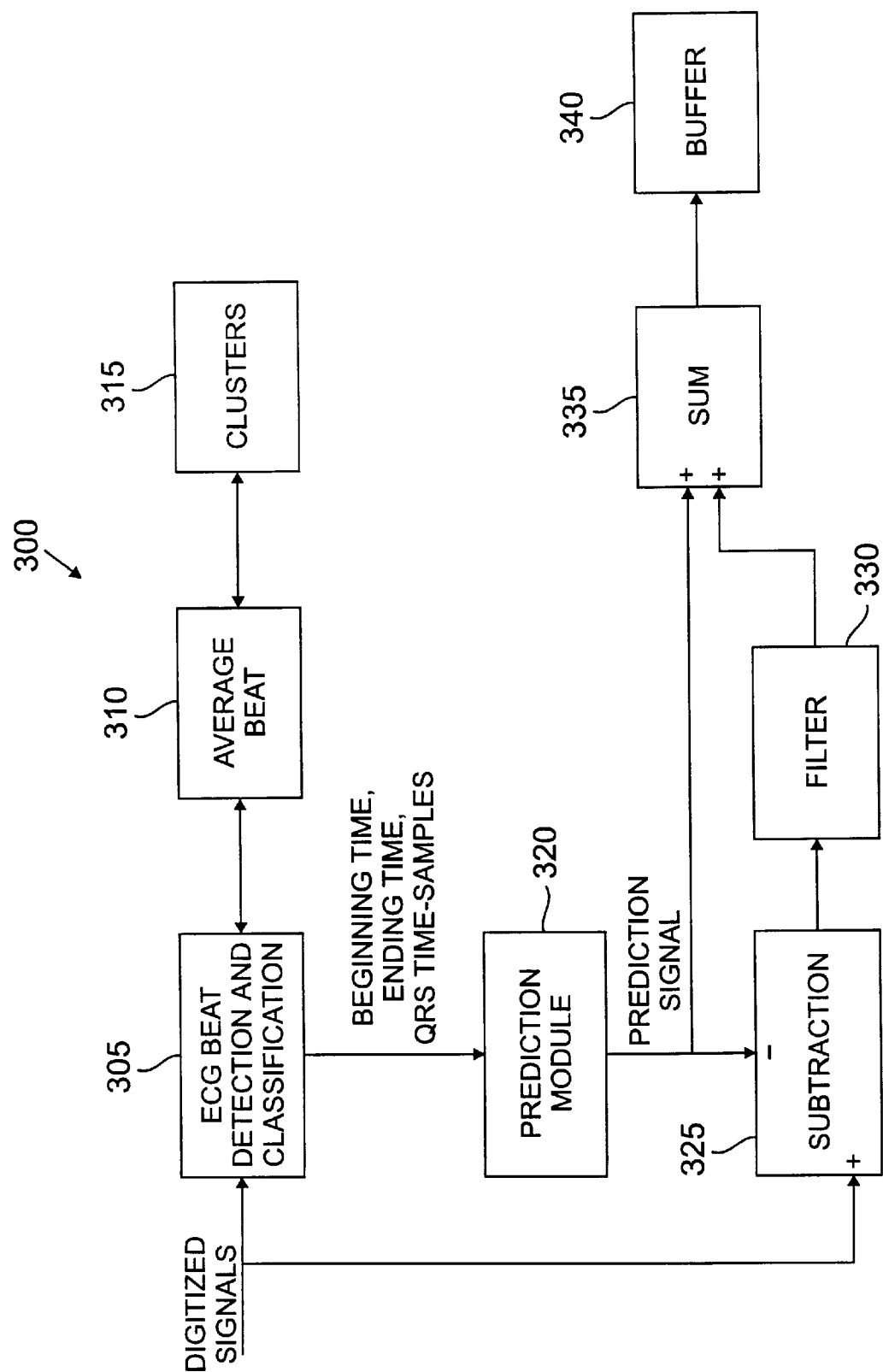
FIG. 3 is a block diagram of a filtering system of the ECG system of FIG. 2.

As one aspect of processing the digitized signals, the processor filters them to reduce noise without significantly reducing the high-frequency content of the QRS complexes of the signals. FIG. 3 illustrates a filtering module 300 of the processor. The module 300 may be implemented using software, dedicated hardware, or a combination of the two.

As shown in FIG. 3, an ECG beat detection and classification module 305 receives the signals from the amplifier module 225. The module 305 detects, delineates and classifies the QRS complexes in the received signals. The detection is performed based on an absolute spatial velocity (ASV) signal derived from ECG signals produced by three approximately orthogonal leads. The ASV signal is defined as:

$$ASVT_t = abs(X_t - X_{t-1}) + abs(Y_t - Y_{t-1}) + abs(Z_t - Z_{t-1}),$$

where the three ECG signals are designated as X, Y, and Z, the subscript t indicates the current time sample, and the subscript t−1 indicates the previous time sample. Alternatively, the ASV signal could be implemented using a single ECG signal or other collections of ECG signals.

The QRS complex for a beat is designated as beginning at the time corresponding to the peak of the ASV signal and ending when the ASV signal remains below a threshold level for a predetermined period of time. A similar approach to beat detection and delineation is described by Simoons in "On-Line Processing of Orthogonal Exercise Electrocardiograms," *Computers and Biomedical Research* 8, 105–117 (1975), which is incorporated by reference.

The beat detection and classification module 305 interacts with an average beat module 310. The module 310 maintains a set 315 of clusters of similarly-shaped beats, and a set of representative beats for each of the clusters, where a set of representative beats includes a representative beat for each input signal (i.e., the signal from each electrode). In the described implementation, the representative beats maintained by the module 310 include values only for the QRS complex. Other implementations may use more or other portions of the PQRST beat.

Upon detecting a beat and identifying the QRS complex of the beat, the module 305 compares the identified QRS complex to each cluster stored by the module 310. In particular, for each cluster, the module 305 generates a correlation coefficient based on a comparison of the QRS complexes of the three orthogonal ECG signals to the representative QRS complex for the cluster. A correlation coefficient, ρ, may be generated as:

$$\rho = \frac{\frac{1}{N}\sum_{t=t_Q}^{t_S}[X_t Y_t Z_t]\begin{bmatrix}CX_t\\CY_t\\CZ_t\end{bmatrix} - [\mu_X \mu_Y \mu_Z]\begin{bmatrix}\mu_{CX}\\\mu_{CY}\\\mu_{CZ}\end{bmatrix}}{[\sigma_X \sigma_Y \sigma_Z]\begin{bmatrix}\sigma_{CX}\\\sigma_{CY}\\\sigma_{CZ}\end{bmatrix}},$$

where $X_t$, for $t = t_Q \ldots t_S$ are the N samples of the QRS complex for the X lead of the input signal, and $\mu_x$, and $\sigma_x$, are, respectively, the mean and standard deviation of $X_r$. The other variables represent the same parameters for the Y and Z leads of the input signal and the orthogonal leads of the cluster (CX, CY, CZ). Other implementations may perform the correlation on a larger part of the waveform, or may use different measures of concordance. After making the comparison, the module 305 identifies the best-matching cluster as being the cluster having the highest correlation coefficient.

If the correlation coefficient computed for the best-matching cluster exceeds a threshold value (e.g., a value in the range from 0.90 to 0.95), then the beat is considered to match the cluster, and the module 310 updates the representative beats for that cluster using the set of input ECG signals for the beat. In one approach to updating a representative beat, the module makes a point-by-point comparison between the new beat and the representative beat. If the magnitude of the difference between corresponding points of the two is less than a maximum amount (e.g., 10 microvolts), then the module replaces the value for the representative beat with the value for the new beat. If the magnitude of the difference exceeds the maximum amount, then the module adjusts the value for the representative beat by the maximum amount. For example, when the maximum amount is 10 microvolts, and the value of a point for the new beat exceeds the value of the point for the representative beat by more than 10 microvolts, the module increases the value for the representative beat by 10 microvolts. Similarly, when the value of a point for the representative beat exceeds the value of the point for the new beat by more than 10 microvolts, the module decreases the value for the representative beat by 10 microvolts.

If a beat does not match any of the clusters (i.e., if the correlation coefficient for the best scoring cluster does not exceed the threshold value), then the module 310 creates a new cluster using that beat. If a new cluster cannot be created because the maximum allowed number of clusters has been reached, the beat is considered to be unmatched.

For each beat, the module 305 provides a prediction module 320 with a beginning time, an end time, and time samples of the QRS complex for each of the ECG signals. If the beat is a matched beat, the time samples are taken from the representative beats for the matching cluster. If the beat is an unmatched beat, the time samples are taken directly from the input ECG signals.

The prediction module creates the predicted signal by joining sequential QRS complexes with a series of constant value time samples inserted between each QRS complex and the following QRS complex. The constant value is set equal to the last time sample of the previous QRS complex. An offset is added to the next QRS complex such that the first sample of the QRS complex is equal to the constant value which precedes it. The resulting predicted signal has no discontinuities.

For each ECG input signal, a subtraction module 325 subtracts the predicted signal from the original ECG signal. The resulting signal, which corresponds to the ECG signal less its expected QRS complex, is provided to a filter module 330.

The filter module 330 implements a sixth order Bessel filter with a cutoff frequency of 15 Hz. Each output of the filter module 330 is provided to a summing module 335 that sums the filtered signal with the corresponding predicted signal to produce a final signal that is provided to an output buffer 340.

The various modules operate asynchronously, creating output signals when input ECG samples and QRS complex information become available. The output buffer permits the processor to provide time samples at a fixed rate that corresponds to the sampling rate of the input signals. The output buffer may, for example, make output signals available for further processing or display synchronously with the sampling clock, but with, for example, a two second delay. Other implementations may perform retrospective analyses. In these analyses, which do not require real time (or delayed real time) outputs, the output buffer may be eliminated.

Figure 4:
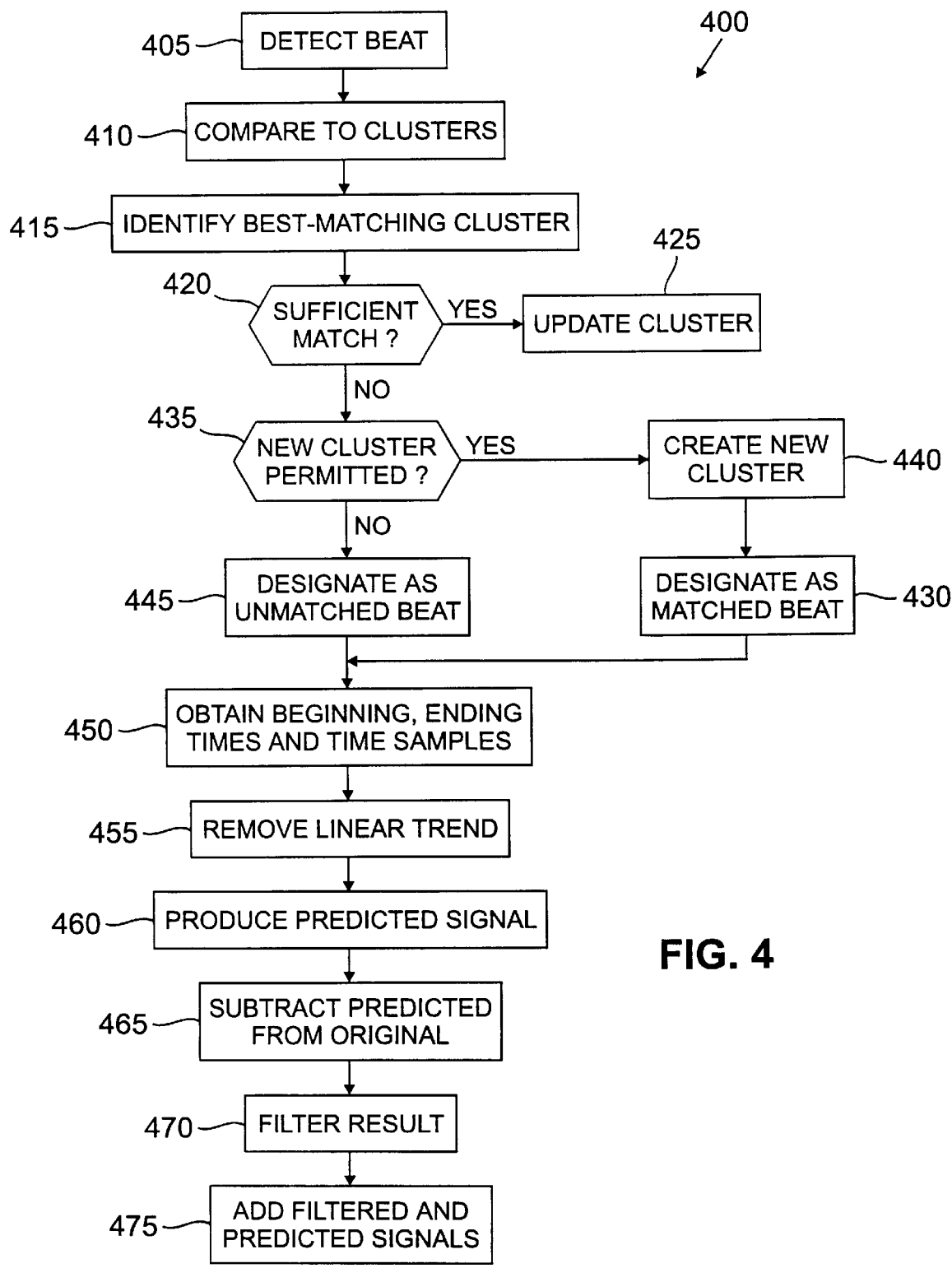
FIG. 4 is a flow chart illustrating a filtering procedure implemented by the ECG system of FIG. 2.

Viewed another way, the processor filters the digitized signals according to the procedure 400 illustrated in FIG. 4. Initially, the processor detects a beat (i.e., a QRS complex) in a digitized ECG signal (step 405). As noted above, the processor may perform this detection by generating and evaluating an ASV signal.

Upon detecting a new beat, the processor compares the new beat to each of a set of one or more stored beat clusters (step 410). As noted above, each cluster may be represented by a representative beat, and the new beat may be compared to a representative beat by generating a correlation coefficient.

After comparing the new beat to all of the clusters, the processor identifies the best-matching cluster (step 415). For example, when the comparison includes generating a correlation coefficient, the best-matching cluster will be the cluster having the highest correlation coefficient.

The processor then determines whether the new beat sufficiently matches the best-matching cluster (step 420). For example, as noted above, the processor may determine whether the corresponding correlation coefficient exceeds a threshold amount. If the new beat matches sufficiently, then the processor updates the cluster using the new beat (step 425) and designates the new beat as a matched beat (step 430).

If the new beat does not sufficiently match the best-matching cluster (step 420), then the processor determines whether an additional cluster may be generated (step 435). If so, the processor creates a new cluster using the new beat (step 440) and designates the new beat as a matched beat (step 430). If not, the processor designates the new beat as an unmatched beat (step 445).

The processor then obtains a beginning time, an ending time, and time samples for the new beat (step 450). If the new beat is a matched beat, the processor obtains the time samples from the cluster that matches the new beat. If the new beat is an unmatched beat, the processor obtains the time samples from the new beat.

The processor then adjusts the provided time samples by adding or subtracting an offset to eliminate discontinuities in the predicted signal, as discussed above (step 455). Using the adjusted samples, the processor produces a predicted signal for the new beat (step 460). The predicted signal has a constant value at times before and after the QRS complex, and corresponds to the adjusted time samples during the QRS complex.

Next, the processor subtracts the predicted signal from the original ECG signal (step 465) and filters the resulting signal (step 470) as described above. The processor then adds the filtered signal to the predicted signal (step 475) to produce a final signal. It will be appreciated that the non-QRS portion of the beat and the difference between the QRS portion of the beat and the QRS portion of the corresponding cluster are filtered in the final signal for a matched beat. For an unmatched beat (or a matched beat for a new cluster), only the non-QRS portion of the beat is filtered in the final signal.

Figure 5A:
FIG. 5A is a graph of an ECG signal.
Figure 5B:
FIG. 5B is a graph of the ECG signal of FIG. 5A after being filtered according to the procedure of FIG. 4.

FIGS. 5A and 5B illustrate an example of an ECG signal filtered using the technique described above. The signal of FIG. 5A represents the unfiltered ECG signal recorded during a period of exercise. The rapid, wavy artifact present in signal 500 is typical of what is seen under such conditions. The signal of FIG. 5B shows the result of using the described filtering technique. As shown, the technique is able to reduce the effects of muscle noise without significantly distorting the QRS complexes.

Other embodiments may implement different strategies for the module 310. For example, a simple module may keep track of a maximum of one type of QRS morphology, with all morphologies other than the dominant morphology being classified as unmatched. The module 310 may use other means of estimating the central tendency of the beat, such as averaging in the time or frequency domain, or may include an adaptive filtering methodology to track changes in the beat morphology.

Other embodiments may create predicted signals by using one or more basis signals for the representative signals. Examples of such basis signals are principal components, wavelets or other orthogonal or non-orthogonal decompositions. The creation of the basis signals may use the biological signal being analyzed or biological signals acquired at other times, or both. The creation of the basis signals may also use signals related to the biological signals. Part or all of a set of basis signals may be used to reconstruct samples of the input signal. By using a partial basis set, features of the signal due to noise are less likely to be reconstructed.

For example, an embodiment may compute the principal components of the QRS complex based on a group of QRS complexes. The components can be computed using QRS complexes of multiple beats or multiple leads, or both. Typically, subsets of the first few principal components are taken as the representative signals. The representative signals and the input signal are used to create measures that quantify how much of each representative signal is present in the input signal. These measures are computed as the projection of the input signal onto the representative signals. The representative signals are combined in proportion to their respective measures, to create a predicted QRS complex.

Other embodiments may use waveforms from the ECG other than the QRS complex. For example, they may use the P wave or the T wave. Still other embodiments may use non-ECG signals or may process signals that are not repetitive in nature.

Other embodiments are within the scope of the following claims.

What is claimed is:

1. A method of reducing noise in a biological signal, the method comprising:
    acquiring a biological signal;
    generating a predicted signal using a representative signal;
    subtracting the predicted signal from the biological signal to produce a second signal;
    applying a filter to the second signal to produce a filtered signal; and
    combining the predicted signal and the filtered signal to produce a noise-reduced signal.

2. The method of claim 1, further comprising comparing the biological signal to the representative signal, wherein generating the predicted signal comprises generating the predicted signal based on results of the comparison.

3. The method of claim 2, further comprising maintaining a set of representative signals corresponding to different groups of biological signals, wherein comparing the biological signal to the representative signal comprises comparing the biological signal to a representative signal for each group of biological signals and selecting a best-matching representative signal.

4. The method of claim 3, wherein generating the predicted signal comprises generating the predicted signal as corresponding to the best-matching representative signal.

5. The method of claim 3, further comprising modifying the best-matching representative signal using the biological signal.

6. The method of claim 2, further comprising, when the biological signal does not sufficiently match the representative signal, generating a predicted signal corresponding to the biological signal.

7. The method of claim 2, further comprising, when the biological signal does not sufficiently match the representative signal, generating a representative signal corresponding to the biological signal.

8. The method of claim 1, further comprising creating a measure using the biological signal and the representative signal, wherein generating the predicted signal comprises generating the predicted signal based on the measure.

9. The method of claim 1, further comprising modifying the representative signal using the biological signal.

10. The method of claim 1, wherein the generating, subtracting, applying, and combining are performed with respect to a particular portion of the biological signal, and wherein the representative signal is based on at least one portion of the biological signal that precedes the particular portion.

11. The method of claim 1, wherein:
    the biological signal comprises a series of beats;
    the generating, subtracting, applying, and combining are performed with respect to a particular beat; and
    the representative beat corresponds to one or more beats occurring prior to the particular beat.

12. The method of claim 1, wherein the representative signal is based on one or more signals related to the biological signal.

13. The method of claim 1, wherein the biological signal comprises an ECG signal.

14. The method of claim 1, wherein the filter comprises a low pass filter.

15. A method of reducing noise in an ECG signal, the method comprising:
    acquiring an ECG signal;
    generating a predicted signal using a representative signal;
    subtracting the predicted signal from the ECG signal to produce a second signal;
    applying a filter to the second signal to produce a filtered signal; and
    combining the predicted signal and the filtered signal to produce a noise-reduced ECG signal.

16. The method of claim 15, further comprising comparing the ECG signal to the representative signal, wherein generating the predicted signal comprises generating the predicted signal based on results of the comparison.

17. The method of claim 16, further comprising maintaining a set of representative signals corresponding to different ECG morphologies, wherein comparing the ECG signal to a representative signal comprises comparing the ECG signal to a representative signal for each ECG morphology and selecting a best-matching representative signal.

18. The method of claim 17, wherein generating the predicted signal comprises generating the predicted signal as corresponding to the best-matching representative signal.

19. The method of claim 17, further comprising modifying the best-matching representative signal using the ECG signal.

20. The method of claim 16, further comprising, when the ECG signal does not sufficiently match the representative signal, generating a predicted signal corresponding to the ECG signal.

21. The method of claim 16, further comprising, when the ECG signal does not sufficiently match the representative signal, generating a representative signal corresponding to the ECG signal.

22. The method of claim 15, further comprising creating a measure using the ECG signal and the representative signal, wherein generating the predicted signal comprises generating the predicted signal based on the measure.

23. The method of claim 15, further comprising modifying the representative signal using the ECG signal.

24. The method of claim 15, wherein the generating, subtracting, applying, and combining are performed with respect to a particular beat of the ECG signal, and wherein the representative beat is based on at least one beat of the ECG signal that precedes the particular beat.

25. The method of claim 15, wherein the representative signal is based on one or more signals related to the ECG signal.

26. The method of claim 16, further comprising detecting a portion of a QRST complex of a beat of the ECG signal, wherein comparing the ECG signal to a representative signal comprises comparing the detected portion of the QRST complex to a corresponding portion of the QRST complex of the representative signal.

27. The method of claim 26, further comprising detecting a QRS complex of a beat of the ECG signal, wherein comparing the ECG signal to a representative signal comprises comparing the detected QRS complex to a QRS complex of the representative signal.

28. The method of claim 27, wherein generating the predicted signal comprises generating the predicted signal as having a QRS complex corresponding to the QRS complex of the representative signal.

29. The method of claim 28, wherein generating the predicted signal comprises generating the predicted signal as having a QRS complex corresponding to the QRS complex of the representative signal, a first constant value at points preceding the QRS complex, and a second constant value at points following the QRS complex.

30. A system for reducing noise in a biological signal, the system comprising:
    means for acquiring a biological signal;
    means for generating a predicted signal using a representative signal;
    means for subtracting the predicted signal from the biological signal to produce a second signal;
    means for applying a filter to the second signal to produce a filtered signal; and
    means for combining the predicted signal and the filtered signal to produce a noise-reduced signal.

31. A method of reducing noise in an ECG signal, the method comprising:
    acquiring an ECG signal;
    maintaining a set of one or more representative signals corresponding to different ECG beat morphologies;
    comparing a beat of the ECG signal to a representative signal for an ECG beat morphology to select a representative signal;
    generating a predicted signal using the selected representative signal;
    subtracting the predicted signal from the ECG signal to produce a second signal;
    applying a low pass filter to the second signal to produce a filtered signal; and
    combining the predicted signal and the filtered signal to produce a noise-reduced ECG signal.

* * * * *

UNITED STATES PATENT AND TRADEMARK OFFICE
CERTIFICATE OF CORRECTION

PATENT NO.    : 5,908,393
DATED         : JUNE 1, 1999
INVENTOR(S)   : PAUL ALBRECHT, PAUL E. GRIMSHAW, AND JEFFREY M. ARNOLD

It is certified that error appears in the above-identified patent and that said Letters Patent is hereby corrected as shown below:

Cover page, [75] Inventors, "Paul G. Grimshaw" should be --Paul E. Grimshaw--.

Cover page, [56] References Cited, OTHER PUBLICATIONS, the "Wildrow" reference, should be the --Widrow-- reference.

Col. 4, at the beginning of the equation at line 24, "ASVI" should be --$ASV_r$--.

Signed and Sealed this

Twentieth Day of March, 2001

Attest:

NICHOLAS P. GODICI

Attesting Officer    Acting Director of the United States Patent and Trademark Office